United States Patent [19]

Jackson

[11] Patent Number: 4,797,209
[45] Date of Patent: Jan. 10, 1989

[54] ADJUSTABLE DISTRIBUTION CELL APPARATUS

[75] Inventor: Derek H. A. Jackson, Tetbury, England

[73] Assignee: Amicon Wright Ltd., Gloucestershire, England

[21] Appl. No.: 129,926

[22] Filed: Dec. 1, 1987

Related U.S. Application Data

[63] Continuation of Ser. No. 881,305, Jul. 2, 1986, abandoned.

[51] Int. Cl.⁴ ............................................. B01D 15/08
[52] U.S. Cl. ...................................... 210/656; 210/95; 210/198.2
[58] Field of Search ............ 210/656, 657, 659, 198.2, 210/95; 55/67, 386

[56] References Cited

U.S. PATENT DOCUMENTS

| | | | |
|---|---|---|---|
| 2,935,194 | 5/1960 | Tomkin | 210/95 |
| 3,372,808 | 3/1968 | Sabo | 210/95 |
| 3,474,908 | 10/1969 | Catravas | 210/198.2 |
| 3,483,986 | 12/1969 | Wright | 210/198.2 |
| 3,487,938 | 1/1970 | Patterson | 210/198.2 |
| 3,777,892 | 12/1973 | Thijssen et al. | 210/198.2 |
| 3,922,223 | 11/1975 | Burkhartsmeier | 210/198.2 |
| 3,966,609 | 6/1976 | Godbille et al. | 210/198.2 |
| 4,361,482 | 11/1982 | Teetz | 210/198.2 |
| 4,597,866 | 7/1986 | Couillard | 210/198.2 |

FOREIGN PATENT DOCUMENTS 8921  8/1979  European Pat. Off. ......... 210/198.2

OTHER PUBLICATIONS

"Moduline TM Industrial Chromatography Column", Operating Instructions (Amicon Corporation, Publication No. 1-287, Jul., 1985), at pp. 3, 10 and 23 to 26.
"Columns for Chromatography", (Amicon Corporation, Publication No. 531, Apr., 1985), at pp. 3, 6, 10, 11, 16 17 and 23.

*Primary Examiner*—Ernest G. Therkorn
*Attorney, Agent, or Firm*—William L. Baker; Bart G. Newland

[57] ABSTRACT

An adjustable distribution cell apparatus is disclosed, the apparatus including first and second independently-operable seals for preventing the leakage of eluant beyond the distribution cell. The inventive apparatus is useful in combination with a chromatographic column having viewing windows therein.

12 Claims, 5 Drawing Sheets

ADJUSTABLE DISTRIBUTION CELL APPARATUS

This is a continuation of application Ser. No. 881,305 filed on July 2, 1986, now abandoned.

BACKGROUND OF THE INVENTION

The present invention relates to an adjustable distribution cell apparatus for chromatogrphic columns, and more particularly to such an apparatus having twin sealing mechanisms adapted to seal a small volume of eluant (mobile phase medium) at working pressure therebetween. This invention also relates to chromatography columns useful with the inventive distribution cell apparatus.

The use of column chromatography to separate chemical compounds is well known. The separation of chemical species occurs due to interaction between the sample, the stationary phase and the mobile phase. The stationary phase is a dispersed medium, with a large surface area, through which the mobile phase is allowed to flow. The chemical nature of the stationary phase exercises the primary control over the separation process; the greater the affinity of a particular chemical compound (the solute) for the stationary medium, the longer it will be retained in the system. Various attraction forces are responsible for retention, including Van de Waals interactions, hydrogen bonding, ionic bonding and reversible complex formation such as the antigen-antibody reaction.

Chromatographic columns are comprised of relatively few parts. A cylindrical column filled with a stationary phase medium is bounded by a bottom cell which permits the mobile phase eluant but not the stationary phase to pass therethrough. A top or "distribution" cell applies the sample and mobile phase across the top of the stationary medium. In many columns the bottom cell is identical to the distribution cell, (in which case both are called "end cells") a configuration which permits the column be run in either direction. Seals must be provided to ensure that the eluant and sample do not leak beyond the end cells and out of the column.

During column chromatography, the mobile phase is percolated through the column by means of gravity or under pressure. High pressure stainless steel industrial columns may operate at up to 3000 p.s.i. (200 kg/cm$^2$), while acrylic, glass and standard stainless steel columns are commonly operated in the range of one atmosphere (approx. 15 p.s.i.) to 4 atmospheres, 3 atmospheres and 6.5 atmospheres, respectively. The choice of stationary phase and mobile phase media of course is critical, but will not be discussed here. Silicas are commonly chosen as stationary phase, although separation of biomolecules, based on size rather than charge, is often accomplished with porous gels. Commonly employed mobile media include the non-polar straight chain hydrocarbons, aromatic hydrocarbons and ethers and ketones of intermediate polarity and the highly polar alcohols and water.

Although column chromatography in the laboratory has long been practiced in glass biurets containing hand-packed stationary phase, the adaptation of column chromatography to large scale industrial separation processes has required the "fine tuning" of the chromatographic technique. For example, it is known that in order to produce accurate separation of the sample it is necessary to distribute the sample uniformly across the top of the column of stationary medium. Moreover, the sample should be distributed directly onto the medium, i.e., with a minimum of "head space" between the top of the medium and the distribution cell which applies the sample thereto. Because the height of the packed column may vary from use to use depending on the chemicals to be separated, or due to swelling or settling of the stationary medium immediately after packing, adjustable distribution cells have won acceptance in history.

U.S. Pat. No. 3,487,938 relates to an "automatic head space reducer" and provides a movable piston which rests on the column of chromatographic medium. The piston automatically follows the top of the column to minimize head space should the bed swell or contract.

U.S. Pat. No. 3,483,986 (A. G. Wright) relates to column chromatography apparatus. Disclosed therein are adjustable end cell apparatus useful for distributing eluant and sample across the top of the column bed. Compressible o-rings form a fluid tight seal around the cells.

Published European Patent Office Patent Application No. 8,921 (A. G. Wright) also discloses adjustable end cell apparatus for chromatographic columns.

As previously mentioned, columns may be manufactured from acrylic, glass or stainless steel. The height adjustment of the distribution cell is easily made in a clear acrylic or glass column as both the top of the column bed and the bottom of the distribution cell are visible. Adjustment of the distribution cell in a stainless steel column is difficult because neither the distribution cell nor the top of the packed bed are visible within the column. To remedy this disadvantage in otherwise desirable stainless steel columns, one aspect of this invention provides a stainless steel column with a plurality of viewing windows disposed therein. These windows are positioned in order to enable the column operator to view the top of the packed bed and to properly position the distribution cell at the top of the bed.

Another aspect of this invention provides an improved adjustable distribution cell apparatus for use with chromatography columns, especially a column with windows. The inventive apparatus provides a seal adjust tube which carries independently operable first and second sealing elements for forming fluid tight seals between the distribution cell and the column tube. A band of eluant, preferably at the working pressure of the column, is allowed to form between the first and second seals and ensures a tight seal in the window region of the column.

DETAILED DESCRIPTION

Figure 1:
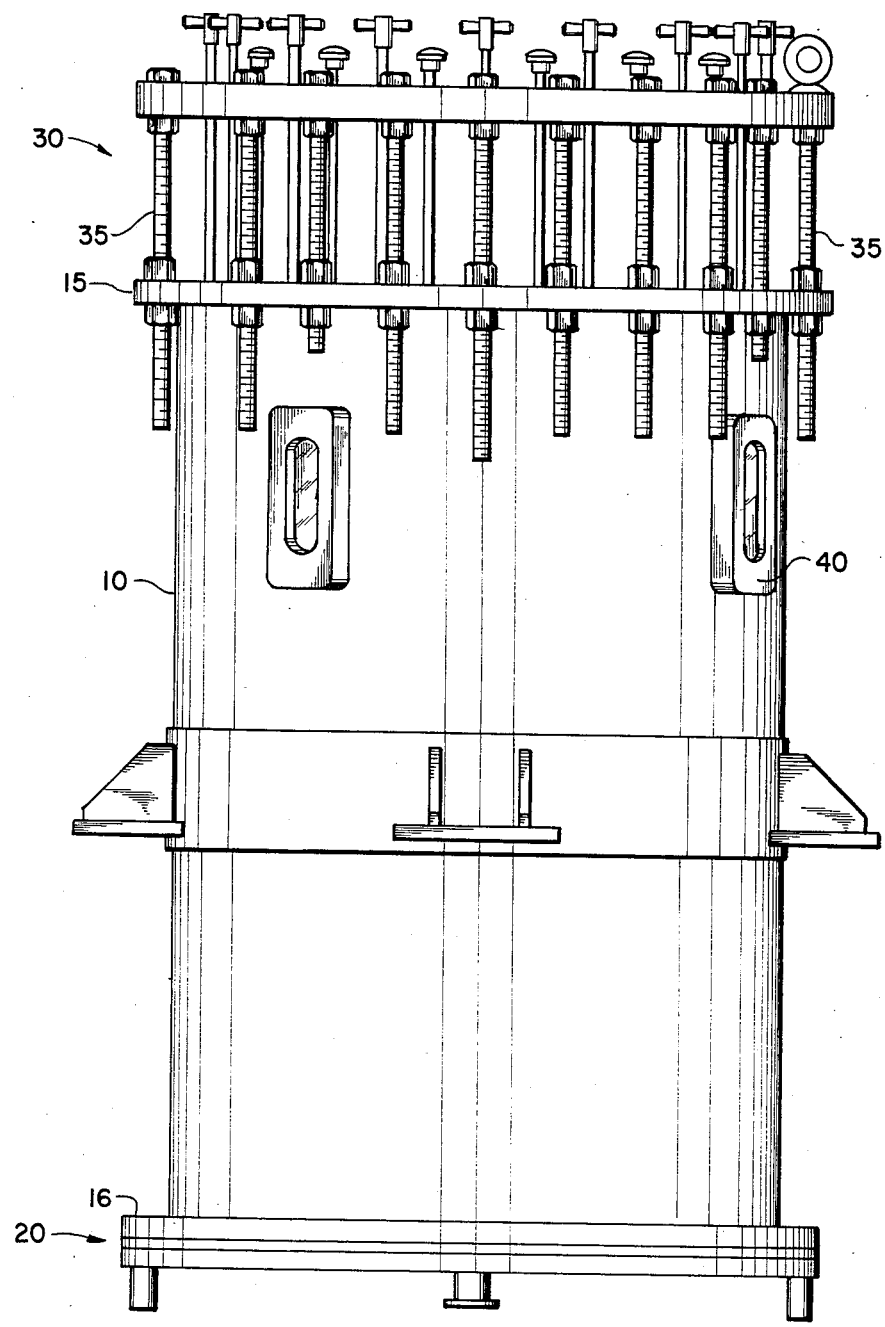
FIG. 1 is a plan view of a chromatographic column and an adjustable distribution cell according to the present invention.

FIG. 1 illustrates a chromatography apparatus comprising a column tube 10 supported on a base 20. The bed of stationary-phase medium contained within the column tube is not shown. Each end of the column tube 10 is fitted with a flange 15, 16, and an adjustable distribution call apparatus 30 according to the present invention is mounted to the upper flange 15 and partially within column tube 10. As seen in FIG. 1, apparatus 30 is mounted on flange 15 of the column tube by a plurality of height adjust rods 35. This illustrated embodiment consists of a stainless steel column tube which includes a plurality of windows 40, the structure and function of which will be explained later.

Figure 2:
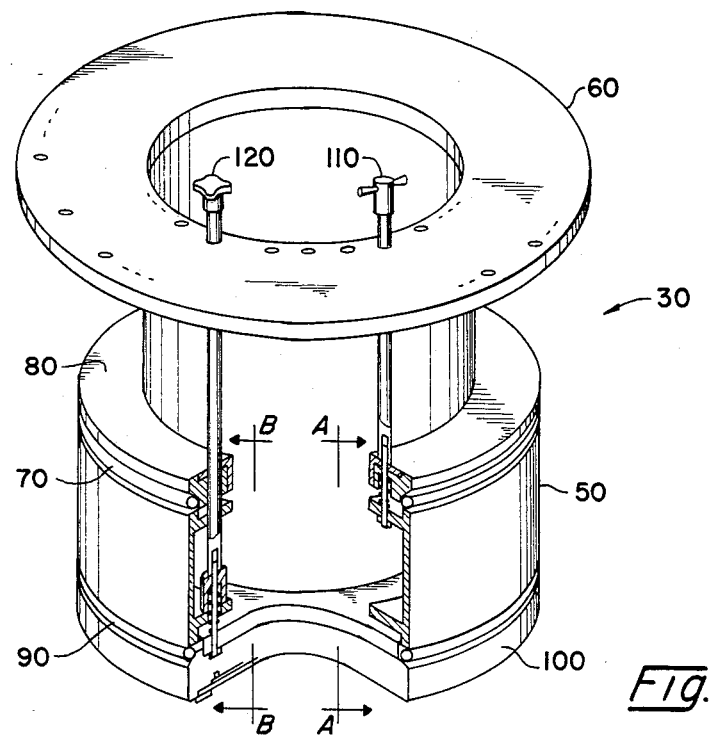
FIG. 2 is a perspective view in partial section of the adjustable distribution cell of FIG. 1.

FIG. 2 illustrates adjustable distribution cell apparatus 30 in greater detail. As seen therein, apparatus 30 consists of a seal adjust tube 50 suspended by a plurality of seal adjust rods from a support collar 60. The seal adjust tube 50 carries two independently operable seals which in this preferred embodiment consist of compressible o-rings. A first seal 70 is disposed in a groove formed between an upper shoulder of the seal adjust tube 50 and seal adjust ring 80. Second seal 90 is disposed in a similar groove formed between a lower shoulder of the seal adjust tube 50 and the distribution cell 100. First and second seals 70, 90 are actuated (i.e., compressed and released) by sets of seal adjust rods 110 and 120, respectively. Only one rod of rod sets 110 and 120 is shown in FIG. 2 for the sake of clarity. Although details concerning the operation of the present apparatus will follow, it will now suffice to say that turning seal adjust rods 110 in one direction causes first seal 70 to be compressed as the seal adjust ring 80 is urged downwardly against the seal adjust tube 50. Second seal 90 is similarly compressed when seal adjust rods 120 are turned to urge the distribution cell 100 upwardly against the seal adjust tube 50.

Figure 5:
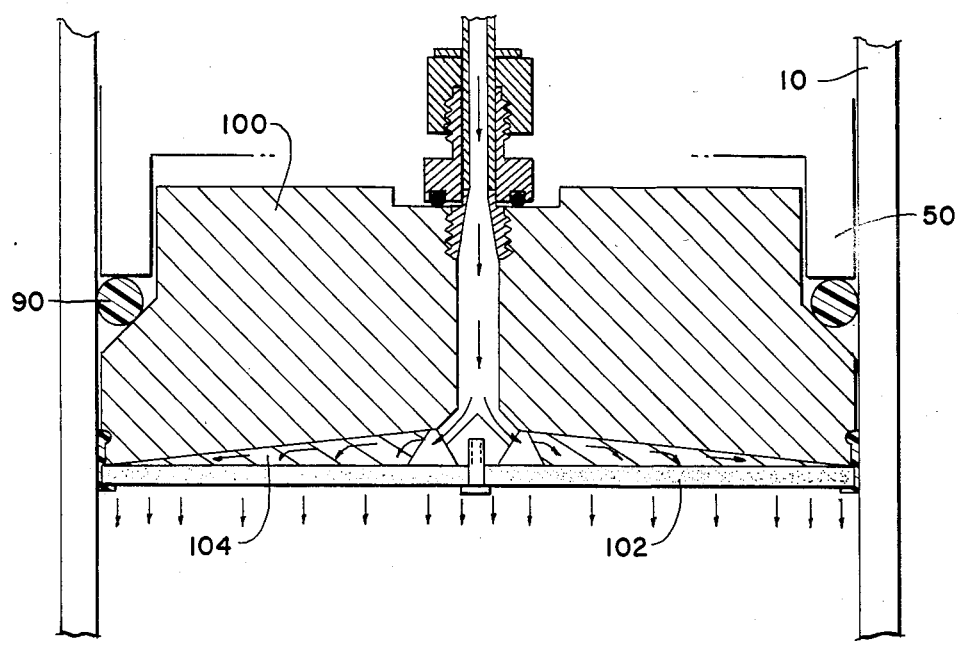
FIG. 5 is a section view of a preferred distribution cell of the inventive apparatus.

Distribution cell 100, as seen in FIG. 5, is in fluid connection with a source of mobile-phase medium and is responsible for evenly distributing the mobile-phase across the top of the packed bed. This preferred distribution cell includes a porous sinter screen 102 overlying a plurality of flow channels 104 formed on the surface of distribution call 100. Mobile-phase medium, as depicted by arrows in FIG. 5, flows along the channels and through the sinter screen onto the packed bed.

Figure 3A:
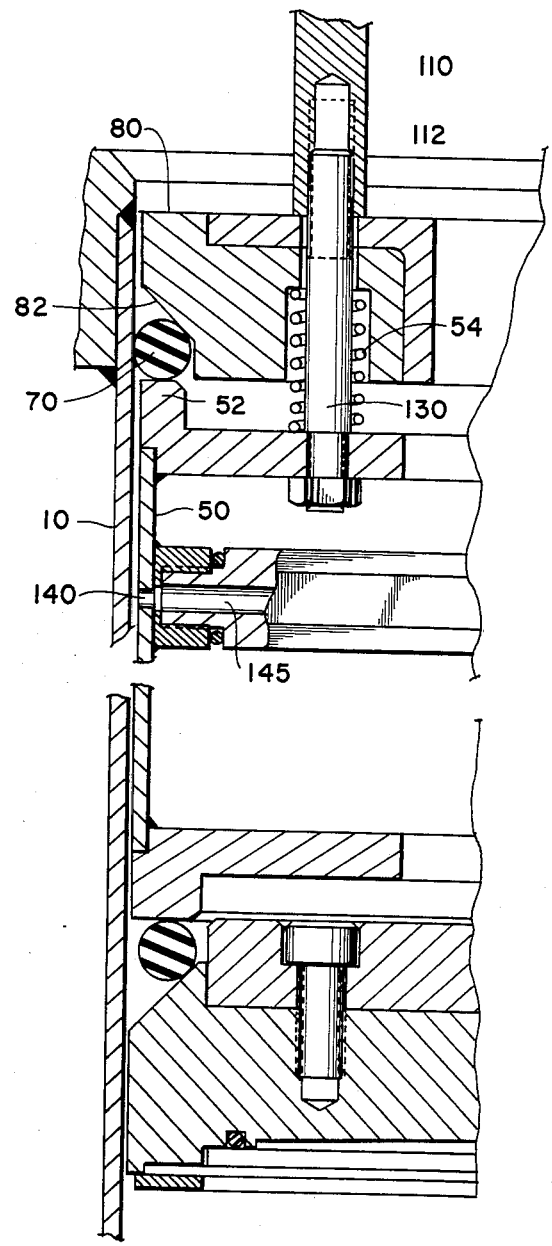
FIGS. 3A and 3B are section views of the adjustable distribution cell of FIG. 2 taken along lines A—A and B—B, respectively.
Figure 3B:
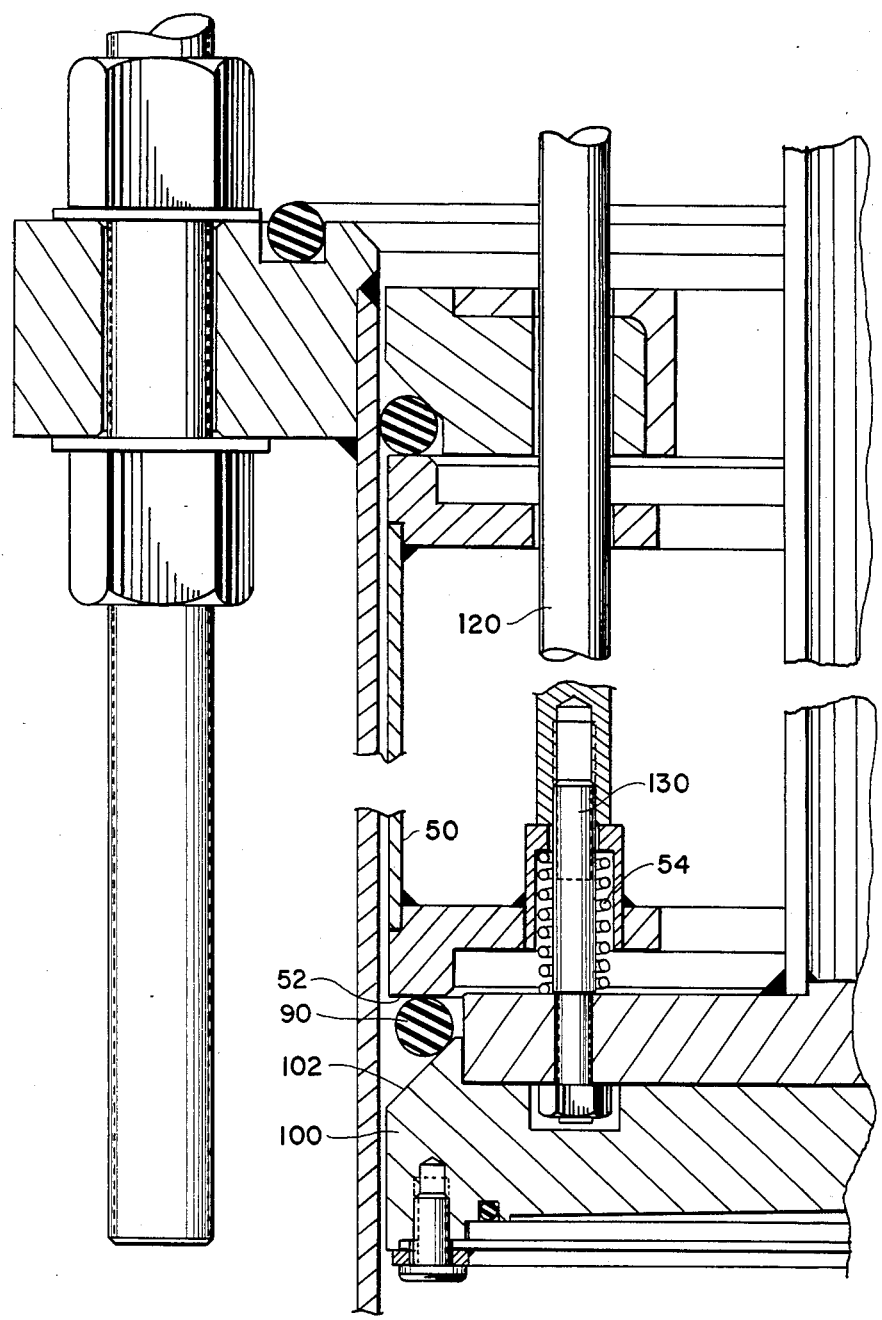

FIGS. 3A and 3B illustrate in greater detail the adjustable distribution cell apparatus of the present invention. As seen in FIG. 3A, seal adjust rod 110 is responsible for adjusting first seal 70 which in this preferred embodiment consists of a compressible, elastomeric o-ring. O-ring 70 is disposed in a groove formed between the upper shoulder 52 of seal adjust tube 50 and a corresponding, bevelled shoulder 82 of seal adjust ring 80. O-ring 70 is shown uncompressed in FIG. 3A and barely touching the inner wall of column tube 10. Compression of the o-ring is accomplished by turning rod 110 in a clockwise manner which causes the threaded end 112 of rod 110 to travel downward over the correspondingly-threaded end of stud 130 and thereby urges together ring 80 and tube 50 against the urging of spring 54. When o-ring 70 is compressed, a substantially fluid-tight seal is formed against the inner wall of column tube 10. Seal 70 is released by turning rod 110 counter-clockwise whereby the end 112 of rod 110 travels upwardly along bolt 130 while spring 54 urges apart tube 50 and ring 80.

As seen in FIG. 3A, seal adjust tube 50 includes an orifice 140 in fluid connection with a channel 145. Channel 145 is adapted to contain a pressure sensing device (not shown) for sensing the pressure of the mobile-phase medium which is trapped between seals 70 and 90 during operation of the column. Orifice 140 should be plugged if a pressure sensing device is not being used.

The mechanism for adjusting the second seal 90 is illustrated in FIG. 3B. Like first seal 70, second seal 90 is disposed between a shoulder 54 of seal adjust tube 50 and a bevelled shoulder 102 of distribution cell 100. Second seal 90 is compressed by turning rod 120 clockwise so that the threaded end of stud 130 and distribution cell 100 are drawn upwardly towards seal adjust tube 50 against the urging of spring 54. Thus, the adjustment mechanisms for first seal 70 and second seal 90 are virtually identical.

Figure 4:
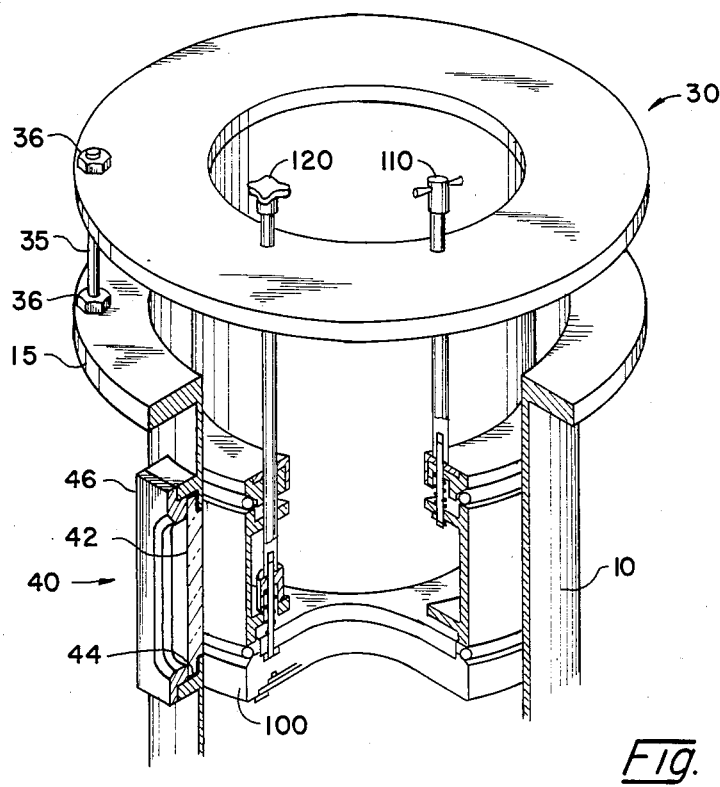
FIG. 4 is a plan view in partial section of the adjustable distribution cell of FIG. 2 installed within a chromatographic column with windows.

FIG. 4 illustrates adjustable distribution cell apparatus 30 installed within the upper end of a chromatography column tube 10. Column tube 10 includes a plurality of viewing windows 40 of which only one is illustrated. As seen in FIG. 4, window 40 comprises a plate 42 of glass or other transparant material installed within a correspondingly-shaped opening in the column tube. A layer of gasketting material 44 is installed between window plate 42 and the wall of column tube 10, and a cover plate 46 is secured to the column tube.

OPERATION

Chromatographic separations are performed in the column of FIGS. 1 and 4 by first preparing a packed bed of stationary-phase medium whereby the top of the bed lies between the top and bottom of the window 40. Means and methods of preparing packed beds are well known. The adjustable distribution cell apparatus 30 is lowered into the column tube 10 while making sure that height adjust rods 35 engage corresponding holes in column flange 15. The distribution cell apparatus 30 is lowered until cell 10 barely touches the top of the bed, and height adjust nuts 36 are tightened to secure apparatus 30 in place. Each of the seal adjust rods 110 are tightened to thereby compress flat seal 70 into fluid tight engagement with the interior wall of column tube 10. Mobile-phase medium is supplied under the desired working pressure to the column via the distribution cell 100, whereupon the mobile-phase medium flows past second seal 90 (which is still uncompressed), along the seal adjust tube 50 and up to the first seal 70. Second seal 90 is then compressed by tightening seal adjust rods 120 to form a fluid-tight seal between the working column bed and the top of the distribution cell. A pressure sensing device installed within channel 145 may be used to verify that the mobile-phase medium trapped between seals 70 and 90 is at substantially the same pressrue as the mobile-phase medium in the column. Should any breach occur in the integrity of first seal 90, the working-pressure volume of eluant trapped between the first and second seals, and ultimately the second seal 70, serves to prevent leakage beyond both seals and out of the column.

The specific example of the invention as herein shown and described is for illustrative purposes only. Various changes in structure and operation may occur to those skilled in the art. For example, the inventive adjustable distribution cell apparatus is well suited for use with chromotography columns without windows and may be operated by compressing only one of the two compressible seals. Such changes will be understood as forming a part of the present invention insofar as they fall within the spirit and scope of the appended claims.

I claim:

1. In combination, an adjustable distribution cell apparatus and a chromatography column adapted to receive said apparatus and comprising a column tube, a bed of stationary phase medium and a mobile phase medium, said apparatus comprising:
   support means for mounting the apparatus onto the column tube and including means for adjusting the height of the apparatus within the column tube;
   second adjustable sealing means suspended from the support means and including a seal-forming element adapted to engage to inside wall of the column tube; and
   first adjustable sealing means, disposed between the second adjustable sealing means and the support means, suspended from the support means and including a seal-forming element adapted to engage the inside wall of the column tube, each of said first and second adjustable sealing means being independently adjustable between a first position, wherein said seal-forming element does not engage the inside wall of the column in a fluid-tight manner, and a second position wherein said seal-forming element engages the inside wall of the column in a fluid-tight manner.

2. An apparatus of claim 1 wherein said first and second sealing means each comprise a compressible seal-forming element which, when compressed, engages the inside wall of the column in a fluid-tight manner.

3. An apparatus of claim 2 wherein said seal-forming elements comprise o-rings.

4. An apparatus of claim 1 wherein said first and second sealing means together comprise a seal adjust tube suspended from the support means by a plurality of seal adjust rods, a first set of said seal adjust rods adapted to adjust said first adjustable sealing means and a second set of said seal adjust rods adapted to adjust said second adjustable sealing means.

5. An apparatus of claim 4 wherein said seal adjust tube includes means for receiving a pressure sensing means.

6. An apparatus of claim 1 further comprising a flow distribution means for distributing the mobile phase medium onto the bed of stationary phase medium.

7. A combination of claim 1 wherein said chromatography column tube includes a window disposed in a side wall of said tube.

8. A method of performing column chromatography comprising providing a column tube, inserting an adjustable distribution cell of claim 1 into the tube, adjusting the first adjustable sealing means to effect a substantially fluid-tight seal, supplying mobile phase medium under working pressure to the column and adjusting the second adjustable sealing means to effect a substantially fluid-tight seal.

9. A method of claim 8 wherein said first and second sealing means together comprise a seal adjust tube suspended from the support means by a plurality of seal adjust rods, a first set of said seal adjust rods adapted to adjust said first adjustable sealing means and a second set of said seal adjust rods adapted to adjust said second adjustable sealing means.

10. A method of claim 9 wherein said seal adjust tube includes means for receiving a pressure sensing means.

11. A method of claim 8 wherein said medium is supplied to the column via a flow distribution means comprising a porous screen overlying a plurality of flow channels.

12. A method of claim 8 wherein said column tube includes a window disposed in a side wall of said tube.

* * * * *